United States Patent [19]
Ronai

[11] Patent Number: 5,741,678
[45] Date of Patent: Apr. 21, 1998

[54] QUANTITATIVE METHOD FOR EARLY DETECTION OF MUTANT ALLELES AND DIAGNOSTIC KITS FOR CARRYING OUT THE METHOD

[75] Inventor: Zeev A. Ronai, Montebello, N.Y.

[73] Assignee: American Health Foundation, Valhalla, N.Y.

[21] Appl. No.: 684,009

[22] Filed: Jul. 23, 1996

Related U.S. Application Data

[60] Continuation of Ser. No. 441,227, May 15, 1995, abandoned, which is a division of Ser. No. 339,786, Nov. 15, 1994, Pat. No. 5,512,441.

[51] Int. Cl.⁶ .............................. C12P 19/34; C12Q 1/68; C07H 21/04
[52] U.S. Cl. .................... 435/91.2; 435/6; 435/91.1; 435/91.53; 435/810; 536/24.33; 935/77; 935/78
[58] Field of Search ............... 435/6, 91.1, 91.2, 435/91.53, 810; 536/24.33; 935/77, 78

[56] References Cited

U.S. PATENT DOCUMENTS 4,800,159  1/1989  Mullis et al. .................... 435/172.3

OTHER PUBLICATIONS

Kahn et al. (1991) Oncogene 6: 1079–1083.
Landgraf et al. (1991) Analytical Biochem. 193: 231–235.
Innis et al. (1990) "PCR Protocols—A Guide to Methods and Applications," Academic Press, Inc., pp. 28–38.

*Primary Examiner*—W. Gary Jones
*Assistant Examiner*—Paul B. Tran
*Attorney, Agent, or Firm*—Ladas & Parry

[57] ABSTRACT

There is disclosed a quantitative sensitive method to enable the detection of point mutations at a known site to a diagnostic kit which uses a multi step (for example, four steps) or a single step reaction. The method uses selective polymerase chain reaction (PCR) amplification of mutant test gene sequences involving first stage amplification of both mutant and wild-type sequences, first stage restriction enzyme digestion of only wild-type sequences, second stage amplification of undigested amplified fragments enriched in mutant sequences and second stage digestion of previously undigested wild-type sequences. Long and short tail primers are used in the first and second stages of amplification respectively to enable selective amplification (in the second stage) of only previously amplified material and none of the original test genomic DNA. The short tail primers are labelled with biotin and fluorescence at their respective 5' and 3' ends to enable easy detection and quantitation of mutations in the test gene via automated fluorescence readers. The use of multi steps as well as a single step reaction is disclosed. The process is exemplified with respect to its use in detecting mutations in the human K-ras gene, yet it is applicable for any given mutation in a defined site.

6 Claims, 3 Drawing Sheets

QUANTITATIVE METHOD FOR EARLY DETECTION OF MUTANT ALLELES AND DIAGNOSTIC KITS FOR CARRYING OUT THE METHOD

This application is a continuation of application Ser. No. 08/441,227, filed on May 15, 1995, now abandoned, which is a division of application Ser. No. 08/339,786, filed on Nov. 15, 1994, now U.S. Pat. No. 5,512,441.

FIELD OF THE INVENTION

The invention relates to methods and respective kits for the early detection of genetic mutations. The methods and kits make use of quantitative sensitive reactions to enable detection of point mutations at known sites.

BACKGROUND OF THE INVENTION

The development of methodologies for the early detection of genetic mutations is an important issue in the prevention and treatment of malignancy. Current knowledge of the association of specific genetic alterations with the development of certain types of tumors enables an approach to the early detection of cancer long before histologic or pathologic evidence indicates the development of neoplastic tumor growth. The identification of genetic alterations as biological markers allows for early diagnosis, which in turn may dictate a particular regimen of treatment to prevent subsequent tumor development.

The multistep process of transformation is thought to be directed by an accumulation of specific dominant and recessive genetic lesions. For example, one frequent dominant event in somatic cell cancers has been found to be an activating mutation in a member of the ras gene family. Strong support exists for the concept that ras oncogenes are causative players in the multistep process of tumorigenesis. Ras gene mutations occur in approximately 15% of human tumors, however their incidence appears to vary according to tumor type. Specifically, mutations in the human K-ras gene have been reported to be as high as 90% in carcinomas of the pancreas, 60% in adenocarcinomas of the lung, and 50% in adenocarcinomas of the colon. In certain tumor types, K-ras gene mutations present themselves as early events in the tumorigenic pathway, and evidence suggests that they are more prevalent during the later stages of tumor development.

The most frequently activated position of the K-ras gene in human tumors has been found to be codon 12. Therefore, by way of example, the detection of mutations at this position could be of critical importance in many aspects of research and diagnostic application. Furthermore, the clinical application of the assay for detection of mutations in biological samples could be of great prognostic value, and could assist in evaluating early courses of patient intervention.

Presently, the detection of mutant genes has been accomplished through the use of the polymerase chain reaction (PCR), a quick and simple in-vitro reaction through which adequate amounts of a specific gene region can be generated for subsequent analysis. Amplified DNA fragments have been analyzed for the presence of point mutations employing one of several technical approaches briefly outlined below:

1. Single-strand conformation polymorphism analysis is a method for analyzing DNA for nucleotide substitutions. In this method, amplified material is denatured to create single-stranded DNA and separated on a native polyacrylamide gel under conditions that enable distinction between single strands of normal and mutant alleles, each migrating at a different rate. This technique can be used to identify alterations in any given gene without requiring knowledge of the specific site where a mutation has occurred.

2. Sequencing an amplified product of a specific gene is an approach that leads to the direct identification of a mutated site. This approach is the most labor-intensive, yet it provides complete information with respect to the type of mutation and its precise location.

3. Restriction fragment length polymorphism where PCR amplified products are digested with specific restriction enzymes which can selectively digest either a normal or a mutated allele or a particular gene. To obtain higher sensitivity, the RFLP has been modified through the incorporation of a liquid hybridization step in which amplified material is hybridized with a labelled oligonucleotide sequence which is specific for a mutated region prior to separation on PAGE. This approach, also known as high resolution RFLP analysis, eliminates the need for sequencing, but it is limited to the analysis of mutations at a precise location that involves a naturally occurring restriction enzyme site. To overcome this limitation, one can artificially introduce restriction enzyme sites to permit a distinction to be made between normal and mutant alleles where the position of the point mutation does not harbor a naturally occurring site. In this approach, base-pair substitutions are introduced into the primers used for the PCR, yielding a restriction enzyme site only when the primer flanks a specific point mutation. This approach enables the selective identification of a point mutation at a known site of presumably any gene.

4. Enriched PCR is a modification introduced by the inventor (collaborating with others) into the RFLP analysis which permits the detection of a mutant gene even when the mutation is present at very low frequency (i.e. 1 in $10^4$ normal alleles). The principle of this approach is to create a restriction enzyme site only with normal sequences, thus enabling selective digestion of normal but not of mutant alleles amplified in a first amplification step. This prevents the non-mutant DNA from further amplification in a second amplification step while, upon subsequent amplification, the mutated alleles are enriched.

5. Mismatched 3' end amplifications is a PCR technique which utilizes 5' primers that have been modified at the 3' end to match only one specific point mutation. This method relies on conditions under which primers with 3' ends complementary to specific mismatches are amplified, whereas wild-type sequences preclude primer elongation. This procedure requires a specific primer for each suspected alteration and must be carried out under rigorous conditions.

The inventor, in collaboration with others, has previously shown that PCR amplification of human K-ras gene first exon sequences can be accomplished using an upstream primer (K5') encoding a G→C substitution at the first position of codon 11 (Jiang et al, Oncogene, 4, 923–928 (1989)). The sequence of K5' thus mediates a BstNI restriction enzyme site (CCTGG) overlapping the first two nucleotides of wild-type codon 12. Since this site is absent from mutuant codon 12 fragments, RFLP analysis of the amplified products can be used to detect K-ras oncogenes activated at codon 12. Importantly, a second BstNI site may be strategically incorporated into the downstream primer (K3') as an internal control for enzyme fidelity.

The principle behind the 'enriched' amplification procedure of the prior art is described in an article co-authored by the inventor (Kahn et al., (1991). Oncogene, 6, 1079–1083) and shown in the schematic flow diagram of FIG. 1. K-ras first exon sequences are PCR amplified using the upstream primer, K5', and a new downstream primer K3' wt which lacks an internal control BstNI restriction site. The 157 nt long fragment is digested with BstNI, thereby cleaving wild type fragments and rendering them inaccessible for subsequent amplification. The products of the digestion, enriched in full length mutated codon 12 sequences, are then used in a second round of PCR amplification with primers K5' and K3'. These samples are subject to RFLP analysis by digestion with BstNI, followed by polyacrylamide gel electrophoresis of the products.

Referring to FIG. 1, in a first round of amplification (A), primers K5' and K3' wt (wild-type) are utilized for the synthesis of a 157 nt fragment including codon 12 sequences. K5' contains a nucleotide substitution at the first position of codon 11, creating a BstNI restriction site (CCTGG) overlapping the first two nucleotides of wild type codon 12 (hatched box). Digestion of PCR amplified sequences from the first round with BstNI leaves uncleaved products enriched in mutant codon 12 sequences (black box). These uncleaved products are subject to a second round of amplification (B) using primers K5' and K3' (containing a control BstNI site; cross-hatched box). Upon RFLP analysis with BstNI, sequences derived from a mutated codon 12 allele show bands of 143 and 14 nt, while amplified wild type allele remnants are cleaved to generate fragments of 114, 29, and 14 nt.

While the enriched PCR and other techniques discussed above provide approaches for the possible early detection of mutant alleles, there are drawbacks in their use for the identification of a mutant allele in a pre-neoplastic lesion. So, for example, in the enriched PCR technique, although it may be desirable to amplify in a second amplification step only duplexes which were formed in a first amplification step, no procedure has been provided to prevent amplification in a second amplification step of genomic DNA which was present in a test sample originally. Another drawback of the enriched PCR technique and the other prior art techniques discussed above is that they are cumbersome and are not easily adapted for use in diagnostic kits. For example, the previously used method for detection of mutant alleles in the enriched PCR technique involves a gel separation of selectively amplified mutant alleles from others. What has been needed is a more sensitive and less cumbersome method of detection that can be easily converted into a diagnostic kit. What has also been needed is a quantitative procedure to enable quantification of the results of a genetic screening. What has further been needed is a simplification of the three stage procedure of the prior art (involving amplification, digestion, re-amplification and final digestion followed by PAGE analysis).

SUMMARY OF THE INVENTION

It is an object of the invention to provide a quantitative assay for the detection of a mutant allele in a pre-neoplastic lesion.

It is another object of the invention to provide a method for amplifying a nucleic acid duplex present in a test sample in a two step amplification process which enables amplification in a second amplification step only of duplexes formed in a first amplification step and thereby prevents amplification in the second amplification step of duplexes which were present in the test sample prior to the first amplification step (e.g., genomic DNA).

It is a further object of the invention to provide a more sensitive assay for the detection of a mutant allele in a test sample.

A still further object of the invention is to provide a quantitative assay for the detection of mutations in a test gene, such as codon 12 of a K-ras gene.

Yet another object of the invention is to provide reagent mixtures which can be used in a diagnostic assay to detect and quantify the presence of mutations in a gene.

It is a still further object of the invention to provide diagnostic kits which may be used easily to detect point mutations in a test gene.

It is also an object of the invention to provide a process which simplifies and affords time savings over the multi-stage processes of the prior art.

To achieve the above and other objects of the invention, there is provided a process for analyzing a nucleic acid test sample taken from the genome of an organism for the detection of a mutant nucleotide sequence in a specific region of the genome, wherein the region can contain the mutant nucleotide sequence even at a frequency of $10^{-5}$. The process comprises:

(i) a first amplification step comprising amplifying material in first and second genomic duplexes present in the test sample in a first polymerase chain reaction in which upstream and downstream long tail primers, comprising upstream primer and downstream primer nucleotide sequences respectively, DNA polymerase, four different nucleotide triphosphates and a buffer are used in a repetitive series of reaction steps involving template denaturation, primer annealing and extension of annealed primers to form first and second synthesized nucleic acid duplexes. Each of the first synthesized nucleic acid duplexes has an upstream end and a downstream end and consists of a first synthesized strand and a first complementary synthesized strand. Each of the second synthesized nucleic acid duplexes has an upstream end and a downstream end and consists of a second synthesized strand and a second complementary synthesized strand. Each of the first and second synthesized strands has a first end portion comprising the upstream primer nucleotide sequences and a second end portion comprising nucleotide sequences sufficiently complementary to the downstream primer nucleotide sequences to anneal therewith. The first synthesized duplexes have the region with a mutant nucleotide sequence, and the second synthesized duplexes have the region with a wild-type nucleotide sequence. The upstream and downstream long tail primers are selected such that nucleic acid strands formed in the first polymerase chain reaction using the upstream and downstream long tail primers can anneal with short tail primers which do not anneal with any nucleic acid strands in the (first or second) genomic duplexes. The long tail upstream primers are also selected such that the second synthesized duplexes have a restriction site which is not present in the first synthesized duplexes due to the presence in the first synthesized duplexes of the region with the mutant nucleotide sequence. The restriction site is cleavable with a first restriction enzyme.

ii) a digestion step comprising treating at least a portion of the test sample with the first restriction enzyme whereby selectively to cleave the second synthesized duplexes while leaving the first synthesized duplexes uncleaved, iii) a second amplification step comprising amplifying material that was subjected to restriction enzyme digestion in step (ii) and remained uncleaved. In this amplification step, upstream and downstream short tail primers are used in a second polymerase chain reaction selectively to re-amplify material which was synthesized in the first amplification step and was not affected by the restriction enzyme in step (ii) since it harbors a mutation in the specific region of the genome. The upstream and downstream short tail primers are selected such that they anneal with the first synthesized complementary and first synthesized strands respectively but do not anneal with strands of the first or second genomic duplexes whereby the upstream and downstream short tail primers can be used in the second amplification step selectively to amplify material in duplexes formed in the first amplification step but cannot amplify material in the first or second genomic duplexes. Each of the upstream short tail primers are labelled with a first substance that binds tightly with a second substance such that upstream ends of the further synthesized duplexes bind to a supporting surface coated with the second substance. Each of the downstream short tail primers are labelled with a downstream label such that downstream ends of the further synthesized duplexes have the downstream label. The second amplification step is performed in a vessel (e.g. microwell plate; Eppendorf tube) having the supporting surface coated with the second substance such that further synthesized duplexes labelled with the first substance contact and bind to the supporting surface, or the process includes a binding step comprising contacting the test sample with the supporting surface coated with the second substance whereby further synthesized duplexes labelled with the first substance bind thereto. The binding step can be performed, for example, after second stage amplification or after a subsequent digestion with the restriction enzyme.

iv) a second digestion step wherein the test sample is again treated with the first restriction enzyme selectively to cleave synthesized duplexes containing regions having the wild-type sequence;

v) a washing step to remove at least downstream portions of cleaved duplexes from the supporting surface; and vi) a detection step comprising assaying for the presence of the downstream label on the supporting surface.

In accordance with the invention, there is also provided a diagnostic kit for use in an assay for detecting the presence or absence on a first genomic nucleic acid strand of a genomic region containing a mutant nucleotide sequence, wherein the genomic region can contain the mutant nucleotide sequence or a wild-type sequence, wherein the first genomic nucleic acid strand is present in a test sample in the form of a first genomic duplex consisting of the first genomic nucleic acid strand and a first complementary nucleic acid strand, and wherein the assay comprises at least a first and a second amplification step. The kit comprises:

a) a first reagent mixture for use in the first amplification step wherein material in the first nucleic acid duplexes is amplified in a polymerase chain reaction with synthesis of a first synthesized duplex having a first synthesized nucleic acid strand and a first complementary synthesized strand. The first reagent mixture comprises upstream and downstream long tail primers. Each of the upstream and downstream long tail primers comprises a complementary primer portion and a non-complementary primer portion. The complementary primer portion of the upstream long tail primers is sufficiently complementary to a first end portion of the first complementary nucleic acid strand to enable the upstream long tail primers to anneal therewith and thereby to initiate synthesis of a nucleic acid extension product using the first complementary nucleic acid strand as a template. The complementary primer portion of the downstream long tail primers is sufficiently complementary to a first end portion of the first genomic strand to enable the downstream primers to anneal therewith and thereby to initiate synthesis of a nucleic acid extension product using the first genomic strand as a template. The non-complementary primer portions of the upstream and downstream long tail primers are not sufficiently complementary to either the first genomic strand or the first complementary nucleic acid strand to anneal with either. The non-complementary primer portions of the respective upstream and downstream long tail primers are positioned on the respective upstream and downstream long tail primers such that a first end portion of the first synthesized strand has nucleotide sequences that are identical to the nucleotide sequences of the non-complementary primer portion of the upstream long tail primers and such that a first end portion of the first complementary synthesized strand has nucleotide sequences that are identical to the nucleotide sequences of the non-complementary primer portion of the downstream primers; and b) a second reagent mixture for use in the second amplification step comprising upstream and downstream short tail primers. Each of the upstream short tail primers has nucleotide sequences which are sufficiently complementary to the nucleotide sequences in the non-complementary primer portion of the upstream long tail primers to anneal therewith but which are not sufficiently complementary to nucleotide sequences in either the first genomic strand or the first complementary genomic strand to anneal therewith. Each of the downstream short tail primers has nucleotide sequences which are sufficiently complementary to the nucleotide sequences in the non-complementary primer portion of the downstream long tail primers to anneal therewith but which are not sufficiently complementary to nucleotide sequences in either the first genomic strand or the first complementary genomic strand to anneal therewith, whereby the upstream and downstream short tail primers can be used in the second amplification step selectively to amplify material in duplexes synthesized in the first amplification step and none of the first genomic duplexes.

Each of the first and second reagent mixtures can also contain four different nucleotide triphosphates, an agent for nucleic acid polymerization under hybridizing conditions and a buffer. The upstream short tail primers of the second reagent mixture can be labelled with a first compound, such as biotin, which binds tightly with a second compound, such as avidin or streptavidin, and the downstream short tail primers of the second reagent mixture can be labelled with a radioactive or fluorescent label.

The kit may be provided with a first microtiter plate which contains the first reagent mixture such that the first amplification step can be performed in the first plate simply by adding the test sample thereto. The kit can also contain a second microtiter plate which is coated with the second compound. The second plate can contain a restriction enzyme which selectively digests synthesized nucleic acid duplexes if a wild-type nucleotide sequence is present in a genomic region of one of the nucleic acid strands of the duplexes. The reaction mixture of the first amplification step, or a portion thereof, can thus be added to the second plate whereupon synthesized duplexes containing a genomic region with a wild-type sequence will be selectively digested. The second reagent mixture can be added to the second plate after the digestion to perform the second amplification step. The second reagent mixture can contain the upstream short tail primers labelled with biotin such that nucleic acid duplexes formed in the second amplification step will bind to the second plate. The kit can contain additional amounts of the restriction enzyme and its buffer so that the duplexes bound to the second plate can be further digested. After such further digestion, the second plate can be washed to remove unbound duplexes such that only uncleaved duplexes having regions with the mutant nucleotide sequence will remain in the second plate. These uncleaved duplexes will have fluorescent or radioactive labels at their downstream ends and can be readily assayed and quantified.

DETAILED DESCRIPTION

Figure 1:
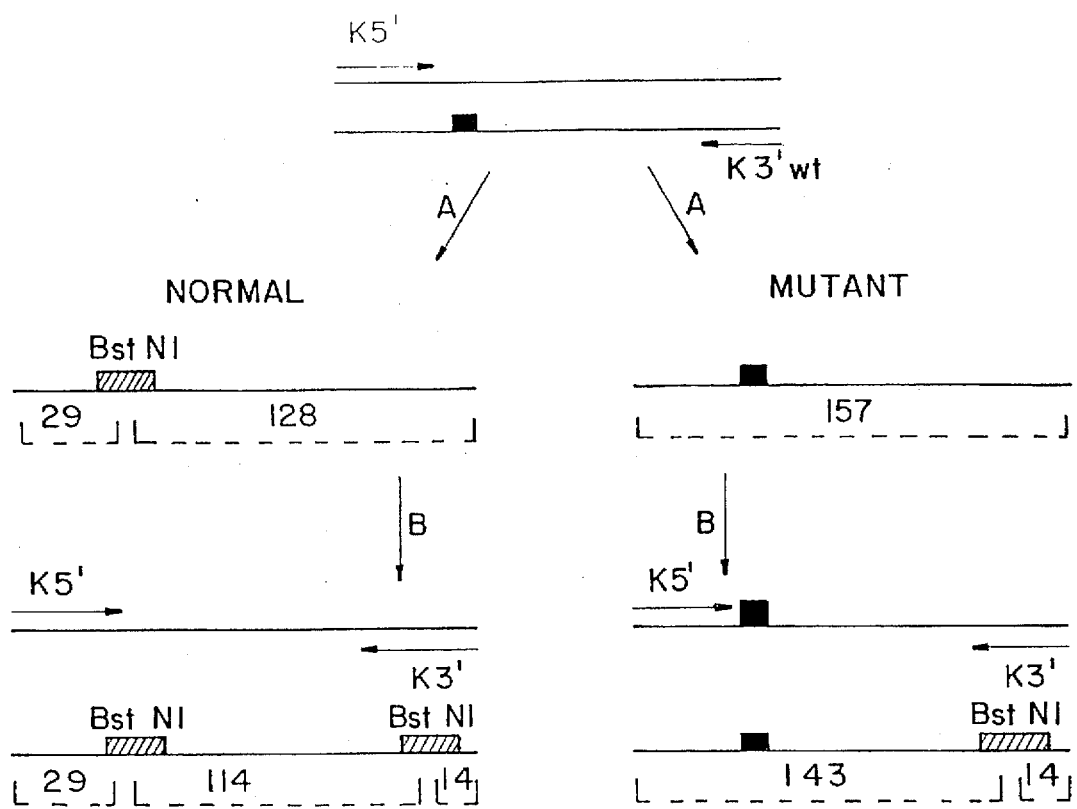
FIG. 1 is a flow chart depicting the enriched PCR procedure of the prior art.

The improved process of the present invention will now be discussed with reference to the figures of the drawing. As will be understood in this discussion, the process can be readily adapted for use in a diagnostic kit. For example, the procedure can be performed in microtiter plates provided in the kit. A set of two plates can be used to complete the process. Each plate can come with its own set of reagents to minimize the need for addition of reagents. Additional steps can be performed using provided solutions (i.e. previously prepared mixtures in separate containers) all on the same plate or plates. With the exception of the last step, which is quantitation on a microtiter plate using, for example, an automated ELISA reader, all steps can be performed in a PCR microcycler.

Figure 2:
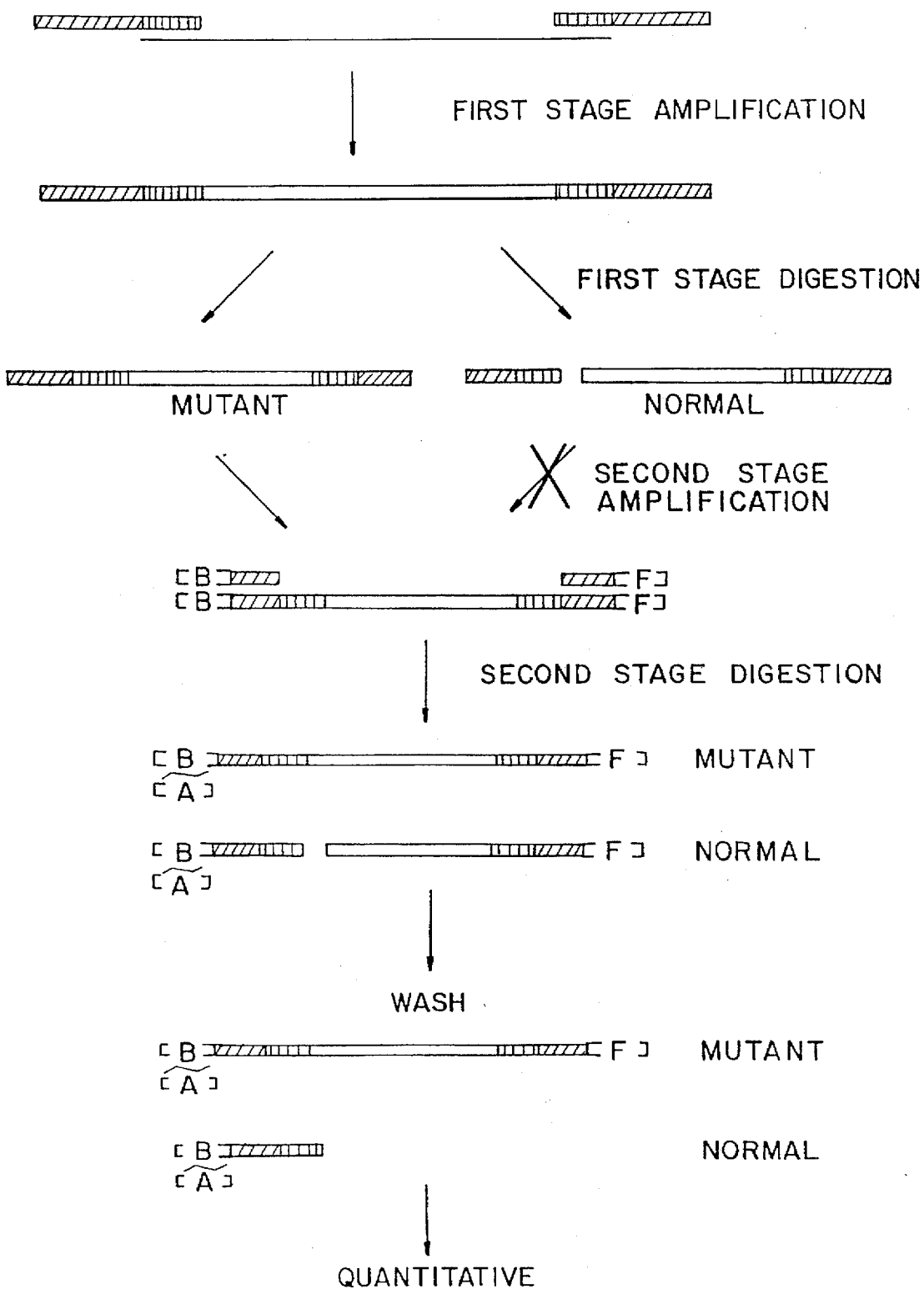
FIG. 2 is a flow chart depicting the steps of the quantitative process of the present invention.

FIG. 2 is a flow chart showing the various stages of a preferred embodiment of the inventive process for detecting a mutation in a target codon of a genomic duplex fragment. In a first stage of the process (see FIG. 2: "First Stage Amplification"), material in the genomic duplex is amplified in a polymerase chain reaction using upstream and downstream long tail primers, each of which comprises a complementary portion which is complementary to one of the nucleic acid strands in the genomic duplex and a non-complementary portion which is not complementary to either of the strands in the duplex. In a preferred embodiment of the invention, a test sample containing genomic DNA duplexes suspected of containing a mutation in a specific codon of one of the strands is added to a first microtiter plate that has a plurality of wells each of which contains a first reagent mix with all reagents necessary for first stage amplification of the duplexes in the test sample. The original test or genomic DNA can be taken for example from a human or other mammal. The source of the DNA can be tissue, biopsy, or body fluids (e.g., blood, effluents, pancreatic juice). The reagent mix includes long tailed primers, dNTPs, a DNA polymerase and its respective buffer. The plate is then placed on a PCR microcycler for first stage amplification of material in the genomic duplexes in a repetitive series of reaction steps involving template denaturation, primer annealing and extension of annealed products to form synthesized DNA duplexes.

After the first stage of amplification, the reaction mix will contain amplified material and genomic DNA. The amplified material consists of the portion of genomic DNA flanked by primers (e.g., 196 base pairs of K-ras codon 12—see Example I, infra), which was multiplied ($\geq 10^6$ times within the first 20 cycles) during first stage amplification. The amplified material includes material which harbors mutation and that which does not. The long tail primers simply add tails to the amplified region. The tails have no effect at this stage of reaction. However, after digestion, the tails will allow amplification of previously amplified material and none of the original genomic DNA.

As will readily be apparent to those of skill in the art, the upstream end portions of the duplexes synthesized in the first amplification stage contain the nucleotide sequences of the upstream long tail primers. The upstream primers can be synthesized or selected so as to mediate a restriction site in a specific codon of a synthesized strand if and only if the codon is present in the strand with the wild-type nucleotide sequence. Products of the first stage amplification may be treated with a specific restriction enzyme which will cleave at the mediated restriction site, and synthesized duplexes containing reagents with the wild-type nucleotide sequences will be selectively cleaved while leaving synthesized duplexes having the codon with a mutant nucleotide sequence uncleaved. Of course, it is important that the synthesized duplexes contain one and only one restriction site for the specific restriction enzyme.

The products of the first stage amplification can be kept as a reference for future needs, with the exception of a portion, for example 5 µl, that can be taken from each of the wells and transferred to a second microtiter plate having a plurality of wells, each of which is provided with a second reagent mix containing the specific restriction enzyme and its respective buffer. The second plate can be placed in the PCR microcycler for a time and at a temperature sufficient for the restriction enzyme to cleave the synthesized duplexes having wild-type sequences in the genomic region (for example, 1 hour at 60° C.). Total volume can be controlled so as not to exceed, for example, 10 µl. This plate can be already coated with avidin, to be used in subsequent steps.

The duplexes synthesized in the first stage amplification are then treated with the specific restriction enzyme in a digestion step (see FIG. 2: "First Stage Digestion"). If the codon contains a wild-type sequence such that the upstream long tail primer mediates a restriction site in the synthesized duplexes, the duplexes will be cleaved by the restriction enzyme during the digestion step, as shown in the duplex labelled "Normal" in FIG. 2. If the codon of the synthesized duplexes contains a mutated nucleotide sequence such that there is no restriction site for the enzyme present in the synthesized duplex, the duplex will not be cleaved by the restriction enzyme during the digestion step and will appear as shown in the duplex labelled "Mutant" in FIG. 2.

A second amplification step is then performed selectively to amplify material in synthesized duplexes which were not digested in the first stage digestion (see FIG. 2: "Second Stage Amplification"). For example, to each well of the second microtiter plate a third mix of reagents can be added.

This mix consists of the reagents necessary to carry out the second stage amplification, including the short tailed primers which are labelled with biotin B on the upstream or 5' primer and fluorescence F on the downstream or 3' primer. Additional polymerase, buffer, and water to adjust total buffer to a desired volume (e.g. 100 μl) can also be part of this mix. The plate will be placed in the PCR microcycler under suitable conditions and for sufficient cycles involving template denaturation, primer annealing and extension of annealed products (e.g., 30 cycles) to effect further amplification.

The upstream and downstream short tail primers used in the second stage amplification can anneal to the respective strands of the duplexes formed in the first stage amplification but cannot anneal to the strands of the genomic duplexes. The upstream short tail primers are synthesized such that they contain biotin B which can bind to a supporting surface coated, for example, with avidin or streptavidin. Downstream short tail primers are labelled with a fluorescent material F (preferably fluorescein) such that strands formed with these primers can be easily detected and quantified in subsequent steps. Techniques for introducing biotin at the 5' or 3' terminus of oligonucleotides are known in the art, as are techniques for replacing dT residues with biotin-dT residues within the oligonucleotide sequence. For example, the literature describes the coupling of a biotin phosphoramidite during oligonucleotide synthesis. A. J. Cocuzza, Tetrahedron Lett., 1989, 30, 6287–6290. The literature also describes products capable of branching to allow multiple biotin additions at the 3' or 5' terminus. P. S. Nelson, M. Kent, and S. Muthini, Nucleic Acids Res. 1992, 20, 6253–6259. Similarly, techniques for the synthesis of fluorescein labelled sequencing primers are known. E.g., F. Schubert, K Ahlert, D. Cech, and A Rosenthal, Nucleic Acids Res. 1990, 18, 3427.

Further synthesized strands formed in the second amplification stage comprise a first end portion with the nucleotide sequences of the upstream short tail primer and a second end portion comprising nucleotide sequences complementary to the nucleotide sequences in the downstream short tail primers. The further synthesized duplexes are labelled with biotin B at their upstream ends and with fluorescence F at their downstream ends.

Following the second stage amplification, the unbound material can be washed away from the plate, thus leaving only the avidin biotin coupled material intact. The further synthesized duplexes are then subjected to a second digestion step (see FIG. 2: "Second Stage Digestion") selectively to cleave duplexes having the region comprising wild-type sequences. To this end, a fourth mix can be added to the plate. This mix can contain new portions of the restriction enzyme along with a suitable buffer. Digestion can be performed for sufficient time to cleave any remaining uncleaved duplexes containing a wild-type region (e.g. 1 hour at 60° C.). Following this step, the plate can be washed and subjected to quantitation via known techniques. Preferably, direct quantitation of the fluorescein signal is made via a fluorescence reader (available commercially). Alternative quantitation procedures include (a) using antibodies against fluorescein which are then detected via known enzyme-linked immunosorbent assay (ELISA) techniques (see, e.g. Landgraf et al, Anal Biochem 198: 86–91 (1991), Alard et al, Biotechniques 15: 730–7 (1993); Kostyn et al, Hum Immunol 38: 148–58 (1993) and Taniguchi et al, J. Immunol Methods 169: 101–9 (1994)); (b) using a radioactive labelled 3' primer and quantitation in a suitable counter, or (c) use of non-labelled 3' primer but, following the second amplification, denaturing the fragment and performing hybridization with a probe which corresponds to the codon 12 mutant allele (or other test region). For example, the denatured fragment can be hybridized with $^{32}$P-labelled or fluorescent probes specific for each possible mutation in codon 12 of the human K-ras oncogene (probes available, e.g., from Clontech, Palo Alto, Calif.). Specific hybridization will add further assurance for the specific quantitation of the mutant alleles and enables a further tenfold increase in sensitivity. The inventor has used the latter approach successfully with radioactive probes for codon 12 of K-ras when the synthesized fragment was immobilized on a nitrocellulose membrane, and has achieved a sensitivity of 1/10$^-$5.

The polymerase chain reaction in each of the amplification steps discussed above can be performed by incubating the test sample at three temperatures corresponding to the three steps in a cycle of amplification—denaturation, annealing and extension. This cycling can be performed automatically, for example, in a PCR microcycler such as the 1605 AirThermo-Cycler (Idaho Technology), or with a DNA Thermal Cycler (Perkin-elmer Cetus Instruments). It can also be performed manually, for example, with pre-set water baths. Typically, the nucleic acid duplexes in the test sample may be denatured by briefly heating the sample to about 90°–95° C., the primers may be allowed to anneal to their complementary sequences by briefly cooling to 40°–60° C., followed by heating to about 70°–75° C. to extend the annealed primers with a suitable agent for polymerization. Suitable agents for polymerization may be any compound or system which will function to accomplish the synthesis of primer extension products, including enzymes. Suitable enzymes for this purpose include, for example, E. coli DNA polymerase I. Klenow fragment of E. coli DNA polymerase I, T4 DNA polymerase, other available DNA polymerases, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be polymerization agents, however, which initiate synthesis at the 5' end and proceed in the other direction, using the same process as described above. A particularly preferred polymerization agent for use in the invention is a thermostable DNA polymerase isolated from *Thermus aquaticus* (known as Taq polymerase) since it can withstand repeated exposure to the high temperatures (90°–95° C.) required for strand separation.

Although conditions for achieving optimal success in polymerase chain reactions can vary, conditions for conducting suitable polymerase chain reactions to amplify nucleic acid (preferably DNA) duplexes in any given test sample of the invention can be routinely derived from standard parameters. By way of example, a standard PCR of the invention may be performed in the first microtiter plate in a buffered solution having a volume of between about 25–150 μl. In addition to a sample DNA, the solution can contain the DNA polymerase (preferably Taq polymerase) in an amount of between about 1.5–5 units (preferably 2.5 units), each deoxynucleotide triphosphate (dATP, dCTP, dGTP and dTTP) in an amount of between about 0.1–0.25 mM (preferably 0.2 mM), and a buffer in an amount of between about 2–15 μl (pending final volume). The buffer will preferably contain 10 mM Tris HCl, pH 8.3, and 50 mM KCl and will be present in an amount sufficient to maintain the solution at a pH of about 7–9. The amount of primer can be carefully quantitated for each amplification step. For example, in the first amplification step, not less than 5 ng and not more than 70 ng (preferably 20 ng) can be used to prevent excess of primers that could be transferred to the subsequent steps (such an excess creates artificial background which should be avoided). The second amplification step can contain a standard excess having, for example, not less than 50 ng and not more than 200 ng (preferably 150 ng) of each primer.

As can be appreciated, in one embodiment of the invention the nucleotide sequences of the respective oligonucleotide primers in the first and second amplification steps are selected such that they are capable of selectively amplifying in the second amplification step PCR material that was synthesized in the first amplification step PCR and none of the genomic DNA. Thus, the second step amplification is selective for the mutant alleles and eliminates background material that could, until now, be synthesized from the original genomic DNA. This is important in applications where, for example, sequences not complementary to a genomic template are added to the 5' end of the primers to provide a means of introducing, for example, restriction sites into the PCR product. This has been achieved using sequences taken from polyoma virus, not present in the human genome.

Once the sequence of a specific region of a target gene is known and the position of a mutation within the region defined, the design of suitable long tail and short tail primers in accordance with the above principles will be routine for those of skill in the art using known techniques. Indeed, to produce specific upstream and downstream long tail oligonucleotide primers each having a portion which is complementary to different strands of a nucleic acid duplex containing desired nucleotide sequences, it is only necessary that a sufficient number of bases at both ends of the sequence be known in sufficient detail so that complementary portions of the upstream and downstream oligonucleotide primers can be prepared which will anneal to different strands of the desired sequence and at relative positions along the sequence such that an extension product synthesized from one primer, when it is separated from its template (complement), can serve as a template for extension of the other primer into a nucleic acid of defined length. The long tail primers are formed such that sequences not complementary to the template are present at the 5' ends of the upstream and downstream long tail primers respectively. These exogenous non-complementary sequences become incorporated into the first stage PCR amplification products and the amplification products thus comprise exogenous end portions on both their upstream and downstream ends. These portions are not present in the original genomic duplexes. The upstream and downstream short tail primers are selected or synthesized so as to anneal only to exogenous end portions whereby they can be used to selectively amplify only material in the PCR amplification products and none of the genomic strands. The long tail primers will preferably be between about 40 and 60 base pairs in length and the short tail primers will preferably be between about 15 and 25 base pairs in length and will overlap the 5' ends of the long tail primers.

Figure 3:
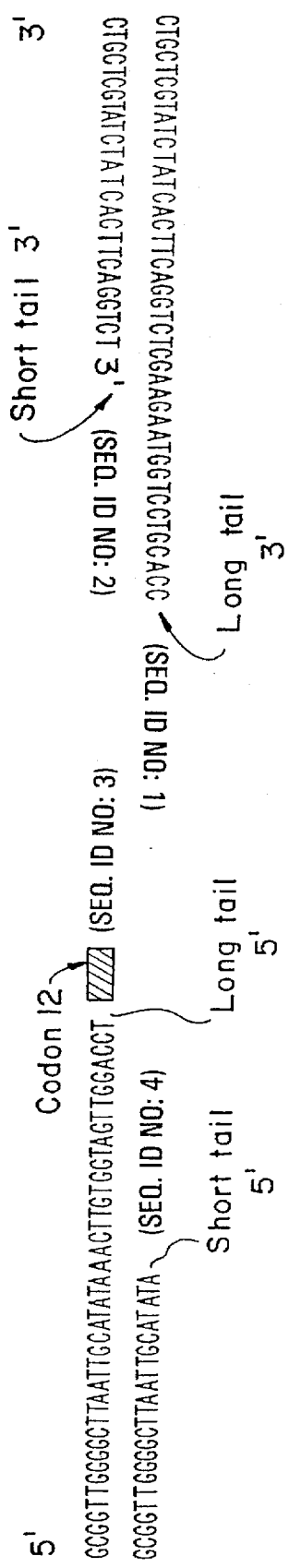
FIG. 3 is a diagrammatic exemplification of long and short tail primers of the invention for use with codon 12 of the human K-ras gene.

The selection of suitable primers will now be exemplified with respect to FIG. 3 which shows long and short tail primers of the invention for use in synthesizing a 196 nucleotide fragment, including codon 12, of the human K-ras gene. As can be seen in FIG. 3 and Example 1 (infra), a preferred upstream long tail primer can consist of 44 nucleotides of which 20 nucleotides overlap the exon sequences of the K-ras gene immediately preceding codon 12. (The upstream long tail primer shown in FIG. 3 is designed to overlap the exon sequences up to, but not including, the nucleotide sequences of codon 12). The upstream long tail primer encodes a G→C substitution at the first position of codon 11. The upstream long tail primer in FIG. 3 thus mediates a BstNI restriction enzyme site (CCTGG) overlapping the first two nucleotides of wild type codon 12 (GG).

The upstream short tail primer shown in FIG. 3 consists of 24 nucleotides which overlap a 24 nucleotide region at the 5' end of the upstream long tail primer. The short tail primer sequences will preferably be derived from polyoma virus DNA, a virus whose nucleotide sequences are not present in the human genome.

The downstream long tail primer shown in FIG. 3 consists of 45 nucleotides which overlap 45 nucleotides at the downstream end of the 196 nt fragment. This primer neither contains nor mediates a BstNI restriction site such that duplexes synthesized using the upstream and downstream long tail primers will be digested by BstNI restriction enzyme only at the recognition site mediated by the upstream long tail primer and only if the test DNA contains wild type sequences at the first and second positions of codon 12.

The downstream short tail primer shown in FIG. 3 consists of 26 nucleotides which overlap a 26 nucleotide region at the 5' end of the downstream long tail primer.

Although the invention has heretofore been discussed with reference to the use of separate plates and/or reaction mixes for the respective steps of amplification digestion and amplification, the invention also encompasses a method wherein the respective steps of amplification, digestion, further amplification, further digestion, etc., are performed in a single reaction mix. In accordance with this aspect of the invention, the inventor has discovered a method for combining, for example, amplification, digestion (selection) and amplification in a single reaction. The prior art reaction was a three step procedure since the reagent used in the digestion step (the restriction enzyme) was not thought to be sufficiently heat stable to withstand the high temperatures which are an integral part of the first and third cycles of PCR amplification (i.e. denaturation and extension). The inventor has now found that, by shortening the cycle times in the polymerase chain reaction and by moderating the high temperatures of the first cycle of the PCR (duplex denaturation), it is possible to preserve the activity of certain restriction enzymes whereby they can be included in the PCR reaction mix without being irreversibly denatured (inactivated). This eliminates the need for a separate reaction mix for each separate stage of amplification and digestion.

Whereas, for a great majority of restriction enzymes, the temperature for optimal activity for a restriction enzyme to cleave DNA is about 37° C., a restriction enzyme for use in the single reaction mix process of the invention will display optimal activity at between about 50° C. and 70° C. and preferably at about 60° C. and above. In any event, a restriction enzyme suitable for use in the one-step process of the invention will be sufficiently thermostable to maintain its activity in cleaving DNA duplexes at the minimum temperatures and cycle times needed to effect amplification of the duplexes in the polymerase chain reaction of the one-step process. Similarly, a polymerase suitable for use in the one-step process of the invention will be sufficiently thermostable to maintain its activity at the temperatures and cycle times used in the process. The restriction enzymes and polymerases that will work in the one-step process of the invention include those restriction enzymes and polymerases that are extracted from thermostable bacteria including *Thermus favus, Thermus ruber, Thermus thermophilus, Bacillus stearothermophilus* (which has a somewhat lower temperature optimum than the others listed), *Thermus aquaticus, Thermus lacteus, Thermus rubens,* and *Methanothermus fervidus.* In addition, thermostable polymerases and restriction enzymes for use in the invention include those isolated from the thermophilic arcaebacteria, such as *Sulfolobus solfataricus, Sulfolobus acidocaldarius, Thermoplasma acidophilum, Methanobacterium thermoautotrophicum,* and *Desulfurococcus mobilis.*

Although as previously noted, temperatures used to denature nucleic acid duplexes in the denaturation cycle of a polymerase chain reaction will typically be between about 90°–95° C., denaturation by heat will occur at temperatures as low as about 88° C. Indeed the inventor has found that, even at the minimal temperatures needed to effect denaturation of nucleic acid duplexes, duplexes can be denatured by heating to such minimal duplex denaturation temperatures and then immediately cooling to the temperatures required for primer annealing. In other words, the duplexes need not be kept at the minimal duplex denaturation temperatures (i.e. they can remain 0 seconds at such temperatures) and denaturation will still occur. Moreover, the inventor has found that, if the duplexes are heated to the minimal temperatures needed for template denaturation sufficiently rapidly (preferably at a rate of between about 5°–20° C./second, and more preferably at about 10° C./second), and are then immediately cooled to primer annealing temperatures sufficiently rapidly (preferably at a rate of at least about 10° C./second), restriction enzymes in the reaction mix having optimal activity at the aforementioned temperatures will not be inactivated during at least the first 10 cycles of the amplification. With respect to the heating of the duplexes to the aforementioned denaturation temperatures, the inventor has found that the upper limit on the rate of heating is limited only by instability which may result between the polymerase and the DNA if the rate is too fast (i.e. it appears that the enzyme dissociates from the DNA when the temperature rises too rapidly).

Similarly, the inventor has found that the nucleic acid extension cycles of a polymerase chain reaction can be conducted at the temperatures required for forming extension products (about 70°–75° C.) without inactivating the restriction enzymes of the invention if the extension cycles are sufficiently rapid. So, for example, such cycles should be conducted for less than 30 seconds at the temperatures required for forming extension products, and will preferably be conducted for less than 15 seconds at such temperatures. The minimum times for the extension cycles will be limited only by the time required for the synthesis of the desired primer extension products. Although this will vary in accordance, for example, with the length of the extension products being synthesized, an extension cycle for the one-step method of the invention may typically last between about 3 to 15 seconds.

To effect the rapid temperature cycles needed to preserve the activity of the thermostable restriction enzymes of the invention during PCR amplification, use may be made of a rapid temperature cycler which operates based on heat transfer by hot air to samples contained in thin capillary tubes. Such cyclers include the 1605 Air Thermo-Cycler commercially available from Idaho Technology of Idaho Falls, Id. This thermocycler uses capillary tubes and air heating to enable transition rates of 5°–10° C./second. Complete 30-cycle reactions can be finished using such cyclers in as little as 10 minutes (see "The 1605 Air Thermo-Cycler User's Guide" published by Idaho Technology).

To optimize the activity of the polymerase and restriction enzyme when included in the same reaction mix, it is necessary to satisfy the buffer requirements of the respective enzymes. Changes to the PCR reaction buffer may affect the fidelity of the polymerase; that is, the polymerase has a certain error rate (incorporating a wrong base pair during DNA synthesis) that may increase if an optimal polymerase buffer is not used. Similarly, the restriction enzymes for use in the invention have buffers that will optimize their activity in cleaving DNA duplexes at or near specific nucleotide sequences. Since optimal buffers for the polymerase and restriction enzymes will differ, combination of the respective enzymes in a one-step reaction requires selection of a buffer that can suitably maintain the activity of each enzyme. Since the fidelity of the polymerase is of prime concern, a suitable buffer for use in the one-step process of the invention will be one that enables the restriction enzyme to cleave duplexes at or near a specific nucleotide sequence without substantially decreasing the degree of fidelity of the polymerase. In this respect, an error rate of $5 \times 10^{-4}$ or less is preferred for purposes of the invention. More preferably, the polymerase error rate will not exceed $1 \times 10^{-4}$. In this respect, some polymerases have higher fidelity than do others, and in certain applications, if a particular polymerase is less than optimal, it may be desirable to use a polymerase with a higher fidelity and a respective suitable buffer.

The preferred polymerases for use with the one-step process of the invention is Taq polymerase. Other suitable polymerases include Vent DNA polymerase (available from New England Biolabs, Beverly, Mass.); Pfu DNA polymerase (available from Stratagene, La Jolla, Calif.) and Altima DNA polymerase (available from Perkin Elmer Cetus, Norwalk, Conn.).

The preferred restriction enzyme for use with the one-step process of the invention is BstNI. Other suitable restriction enzymes which could be "tailored" to other target sequences designed for a given point mutation include Ban I, Bcl I, BsmI, BssH II, BstXI, and Sfi I. These enzymes are all commercially available (from, for example, Stratagene) and have 50°–60° C. as optimal digestion temperature and their recognition sites are known.

Suitable buffers for use in the one-step reaction of the invention can be prepared, for example, by modifying a buffer known to be suitable for the respective polymerase or restriction enzyme used in the reaction. For example, the inventor has found in a preferred embodiment of the one-step process of the invention wherein Taq polymerase is used in the amplification of 196 nucleotide fragment containing codon 12 of the human K-ras gene and the amplification product s are digested with BstNI (see Example II, infra), a suitable reaction mix can contain a buffer consisting of between about 60–80% (preferably 80%) of BstNI buffer. (BstNI buffer, as used herein, consists of 50 mM NaCl, 10 mM Tris-HCl, 10 mM $MgCl_2$, 1 mM DTT (pH7.0) and BSA (100 μg/ml); 80% of BstNI buffer is BstNI buffer diluted with water to 80% of its original concentration). The reaction mix in the preferred embodiment can also comprise between about 5–30 ng of long tail primers (preferably about 20 ng), between about 50 and 150 ng of short tail primers (preferably about 100 ng); between about 7.5 and 10 units of Taq polymerase (preferably 7.5 units); between about 2.5–7.5 units (preferably 5 units) of BstNI enzyme; about 1

μg of test DNA and about 0.2 mM dNTPs. The ratio of long tail primers to short tail primers will preferably be between 3:1 and 6:1, and will more preferably be about 5:1.

If the activity of the restriction enzyme with a certain buffer is not sufficient to cleave nucleic acid duplexes at or near specific nucleotide sequences with a desired efficiency (for example, about 90–95%), additional digestion steps can be added to the reaction.

Following amplification in this are step reaction, material is subjected to analysis via binding to avidin coated matrix followed by fluorescent measurement. The short 3' (tailed) primer does not contain a restriction enzyme site for BstNI (since such a site would not enable further amplification). To control background of normal amplifiable material, a threshold value is established in each reaction using normal or normal diluted with mutant DNA in different ratios (i.e. a calibration curve can be made). The latter also serves as a reference for quantitation of mutant allele incidence.

The present processes and kits can be used for the detection of a mutant allele in any given gene as long as: a) the sequence of the target gene is known and b) the position of the mutation is defined. While a different set of primers has to be designed for each target site, and a different restriction enzyme may have to be used, the principle and the methodology will remain the same. For example, this invention can be used for the analysis of specific point mutations in the p53 tumor suppressor gene, and in particular, in so-called "hot spots" in the p53 tumor suppressor gene. These hot spots include (1) codon 249 which is a hot spot for the potent carcinogen aflatoxin (2) codon 248 which is a hot spot for N-ethyl-N-nitrosourea and (3) codon 393 which is a hot spot of UV in sunlight.

As another example, the present invention can be used for the analysis of specific point mutations in the ras oncogene family in each of the known sites for mutations, which include H-ras, K-ras and N-ras genes at codons 12, 13, and 61. Table 1 exemplifies restriction enzymes that may be used in the process of the invention with respect to each of these genes. The process of the invention is believed to be especially important for assaying codon 12 of K-ras, since it is the most frequent mutation in human colon and pancreatic tumors.

EXAMPLE I

Amplification and Digestion of Fragment of Human K-ras Gene Using Long and Short Tail Primers The methods and kits of the invention will now be exemplified with respect to their use in the amplification and digestion of test DNA including sequences of codon 12 of the human K-ras gene.

A. Sequence of primers used for PCR amplification of sequences of codon 12 of the human K-ras gene:

Downstream long tail primer (45 mer)

5' CTG CTC GTA TCT ATC ACT TCA GGT CTC GAA GAA TGG TCC TGC ACC 3' (SEQ ID NO:1)

Downstream short tail primer (26 mer)

5' CTG CTC GTA TCT ATC ACT TCA GGT CT 3' (SEQ ID NO:2)

Upstream long tail primer (44 mer)

5' GCG GTT GGG GCT TAA TTG CAT ATA AAC TTG TGG TAG TTG GAC CT 3' (SEQ ID NO:3)

Upstream short tail primer (24 mer)

5' GCG GTT GGG GCT TAA TTG CAT ATA 3' (SEQ ID NO:4)

FIG. 3 shows the relative positioning of the respective long and short tail primers with respect to codon 12 of the test fragment.

B. Conditions for amplification and digestion reactions.

First step amplification is performed using 1 μg of test DNA, 2.5 units of Taq enzyme (Perkin Elmer-Cetus, Norwalk, Conn.), 5 μl of Taq buffer (50 mM KCl, 10 Mm Tris-HCl, pH 8.3, 0.01% gelation) 0.2 mM dNTPs, 20 ng of long tail primers (downstream and upstream) 3 mM $MgCl_2$ in a total volume of 50 μl. 20 cycles of amplification are performed using 3 steps for each cycle, composed of 1' @ 94° C., 1' @ 53° C., 1' @ 72° C.

A 5 μl aliquot of the first step amplification reaction is taken into a restriction enzyme reaction in which 5 units of the restriction endonuclease BstNI (purchased from New England Biolabs, Beverly, Mass.)) is added and supplemented with a 1 μl of the BstNI buffer (50 mM NaCl, 10 mM Tris-HCl, 10 mM $MgCl_2$, 1 mM DTT (pH 7.9) and BSA (100 μg/ml) to a total volume of 10 μl. This step is performed at 60° C. for 1 hour.

2 μl of digested material are added to a 100 μl of reaction volume which consist of: 150 ng of short tailed primers, 2.5 units of Taq enzyme, 10 μl of Taq buffer (10×), 0.2 mM dNTPs. Second step amplification is performed for 35 cycles, consisting of 3 steps each 1' @ 94° C., 1' @ 59° C., 1' @ 72° C.

Short tailed primers added to this reaction are labelled with biotin (5' or upstream tail) and fluorescein (3' or downstream tail). This labelling is performed according to chemistry available commercially (from, for example, Milligen Biosearch, Bedford, Mass. and Glen Research Sterling, Va.) during the synthesis of the oligonucleotide in a DNA synthesizer. These modified oligonucleotides can also be purchased.

Following the second step amplification, the material is added to an avidin coated matrix, and digested again with BstNI. Fluorescein measurement is then taken using a fluorescence reader.

C. Diagnostic Kit for Reactions

For kit purposes two microplates and 3 sets of pre-made solutions are utilized.

(1) Microplate A is a plain PCR compatible microplate.

(2) Microplate B is as in (1), but pre-coated with avidin.

(3) Solution A—consists of all reagents required to perform the first step amplification with the exception of test DNA (or control DNA). It therefore contains Taq enzyme, buffer, dNTP, and the long tail primers.

Solution B—consists of reagents required to perform the intermediate digestion step. It contains both the restriction enzyme and its respective buffer.

Solution C—consists of all reagents required to perform second step amplification. It therefore contains short tailed primers labelled with biotin or fluorescein, respectively, enzyme, buffer, and dNTPs.

D. Robotic PCR

The reaction mixes developed for the processes of the invention, such as Solutions A, B and C (above), are easily adapted for use in robotic PCR processes. For Example, a portion of the first stage amplification product of the invention can be transferred by an instrument (robot) to a second vessel which contains the restriction enzyme reaction for first stage digestion. A portion of the product of first stage digestion can be transferred by the instrument to a third vessel containing the reagents for second stage amplification. A portion of the product of second stage amplification can be transferred by the instrument to a fluorescence reader, which can be a part of the instrument. Thus, in this Example, first stage amplification can be conducted in Microplate A by introducing the test DNA and Solution A into the microplate. Then, Solution B can be added to the microplate for first stage digestion. The test sample, or a portion thereof, can then be removed and reamplified in Microplate B with Solution C (containing the short tail primers). Further digestion can be performed in Microplate B with Solution B following which the instrument can carry out the quantitation step in the fluorescence reader.

EXAMPLE II

Multiple Stages of Amplification and Digestion in Single Reaction Mix

A. There is now exemplified a process in which the repetitive cycles of amplification and digestion of Example I are performed in a single reaction. The following have been modified to perform such a reaction.

(1) Reagents (a) buffer is adjusted to enable both digestion and amplification and consists of 80% of BstNI buffer (i.e. BstNI buffer diluted with water to 80%). (b) Primers—20 ng of long primers are mixed with 100 ng of short tailed primers. (c) 7.5 units of the Taq enzyme is used (d) 5 units of BstNI enzyme. (e) all other reagents—DNA; dNTPs;—remain the same as in Example I.

(2) Total volume reduced to 10 µl and reaction is performed in capillary glass tubes.

(3) Reaction is performed in a Hot Air microcycler (the 1605 Air Thermo-Cycler available from Idaho Technology) under the following conditions.

a) hot start—heat test DNA at 88° C. for 10 seconds.
b) 5 cycles consisting of a) 0 seconds @ 88° C., b) 5 seconds @ 53° C., c) 15 seconds @ 72° C.
c) 1 cycle of 60° C. for 20 minutes.
d) 5 cycles as in b.
e) 1 cycle of 60° C. for 20 minutes.
f) steps b–c are repeated once more.
g) 20 cycles consisting of 0 seconds at 88° C.; 5 seconds at 33° C.; and 15 seconds at 72° C.
h) material is taken from capillary glass to microplate coated with avidin.
i) quantitation is then performed as set forth in Example I.

Total time for single step reaction is less than 90 minutes.

B. Diagnostic Kit for Single Step Reaction

It may be appreciated that, for use with a single step reaction, a diagnostic kit of the invention (including a suitable thermostable restriction enzyme, DNA polymerase and buffer) need contain only a single PCR compatible glass tube which is pre-coated with avidin. The kit may contain a single pre-made solution containing the reagents of Section A(1) of this Example.

In summary, the present invention is seen to provide processes and diagnostic kits for analyzing a nucleic acid test sample taken from the genome of an organism. The processes described herein involve less cumbersome techniques and/or require fewer steps to carry out amplification and digestion than do the procedures previously described.

Other modifications of the above-described embodiments of the invention that are obvious to those of skill in the area of molecular biology and related disciplines are intended to be within the scope of the following claims.

I claim:

1. A diagnostic kit for use in an assay for detecting the presence or absence on a first genomic nucleic acid strand of a genomic region containing a mutant nucleotide sequence, wherein said genomic region can contain the mutant nucleotide sequence or a wild-type sequence, wherein said first genomic nucleic acid strand is present in a test sample in the form of a first genomic duplex consisting of the first genomic nucleic acid strand and a first complementary nucleic acid strand, and wherein the assay comprises at least a first and a second amplification step, said kit comprising:

a) a first reagent mixture for use in the first amplification step wherein the first nucleic acid duplexes are synthesized in a polymerase chain reaction with synthesis of a first synthesized duplex, said first mixture comprising upstream and downstream long tail primers, each of said upstream and downstream long tail primers comprising a complementary primer portion and a non-complementary primer portion, the complementary primer portion of the upstream long tail primers being sufficiently complementary to a first end portion of the first complementary nucleic acid strand to enable the upstream long tail primers to anneal thereto and thereby to initiate synthesis of a nucleic acid extension product using the first complementary strand as a template, the complementary primer portion of the downstream long tail primers being sufficiently complementary to a first end portion of the first genomic strand to enable the downstream primers to anneal thereto and thereby to initiate synthesis of a nucleic acid extension product using the first genomic strand as a template, the non-complementary primer portions of said upstream and downstream long tail primers not being sufficiently complementary to either the first genomic strand or the first complementary strand to anneal with either, the non-complementary primer portions of the respective upstream and downstream long tail primers being positioned on the upstream and downstream long tail primers such that a first end portion of the first synthesized strand of synthesized duplexes formed using the upstream and downstream primers has nucleotide sequences that are identical to the nucleotide sequences of the non-complementary primer portion of the upstream long tail primers and such that a first end portion of the first complementary synthesized strand of synthesized duplexes formed using the upstream and downstream primers has nucleotide sequences that are identical to the nucleotide sequences of the non-complementary primer portion of the downstream primers, and b) a second reagent mixture for use in the second amplification step comprising upstream and downstream short tail primers, each of said upstream short tail primers comprising nucleotide sequences which are sufficiently complementary to the nucleotide sequences in the non-complementary primer portion of the upstream long tail primers to anneal thereto but which are not sufficiently complementary to nucleotide sequences in either the first genomic strand or the first complementary genomic strand to anneal thereto, each of said downstream short tail primers comprising nucleotide sequences which are sufficiently complementary to the nucleotide sequences in the non-complementary primer portion of the downstream long tail primers to anneal thereto but which are not sufficiently complementary to nucleotide sequences in either the first genomic strand or the first complementary genomic strand to anneal thereto, whereby the upstream and downstream short tail primers can be used in the second amplification step selectively to amplify synthesized duplexes synthesized in the first amplification step and none of the first genomic duplexes.

2. A kit as claimed in claim 1, wherein the upstream short tail primers are labelled with biotin and the downstream short tail primers are labelled with a fluorescent label.

3. A kit as claimed in claim 2, wherein the kit further comprises a microtiter plate coated with avidin or strepavidin.

4. A kit as claimed in claim 2 wherein each of the first and second reagent mixtures further comprises four different nucleoside triphosphates, a DNA polymerase and a buffer.

5. A kit as claimed in claim 3, wherein the kit further comprises a first microtiter plate comprising the first reaction mixture.

6. A reagent mix for use in amplification of nucleic acid duplexes, said reagent mix comprising a thermostable nucleic acid polymerase, a thermostable restriction enzyme which selectively cleaves the nucleic acid duplexes if and only if the duplexes contain a specific nucleotide sequence, upstream and downstream primers for annealing to each strand of the nucleic acid duplexes whereby to initiate formation of nucleic acid extension products, four different nucleotide triphosphates, and a buffer suitable for enabling the restriction enzyme to cleave duplexes containing the specific nucleotide sequence and for enabling the polymerase to catalyze formation of the nucleic acid extension products.

\* \* \* \* \*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 45
( B ) TYPE: Nucleotide
( C ) STRANDEDNESS: Double
( D ) TOPOLOGY: Linear ( x i ) SEQUENCE DESCRIPTION: SEQ ID NO:1:

CTG CTC GTA TCT ATC ACT TCA GGT CTC GAA GAA TGG TCC TGC ACC      45

( 2 ) INFORMATION FOR SEQ ID NO:2:

( i ) SEQUENCE CHARACTERISTICS:
( A ) LENGTH: 26
( B ) TYPE: Nucleotide
( C ) STRANDEDNESS: Double
( D ) TOPOLOGY: Linear ( x i ) SEQUENCE DESCRIPTION: SEQ ID NO:2:

CTG CTC GTA TCT ATC ACT TCA GGT CT      26

( 2 ) INFORMATION FOR SEQ ID NO:3:

( i ) SEQUENCE CHARACTERISTICS:
( A ) LENGTH: 44
( B ) TYPE: Nucleotide
( C ) STRANDEDNESS: Double (D) TOPOLOGY: Linear (xi) SEQUENCE DESCRIPTION: SEQ ID NO:3:

GCG GTT GGG GCT TAA TTG CAT ATA AAC TTG TGG TAG TTG GAC CT    44

(2) INFORMATION FOR SEQ ID NO:4:

(i) SEQUENCE CHARACTERISTICS:
        (A) LENGTH: 24
        (B) TYPE: Nucleotide
        (C) STRANDEDNESS: Double
        (D) TOPOLOGY: Linear (xi) SEQUENCE DESCRIPTION: SEQ ID NO:4:

GCG GTT GGG GCT TAA TTG CAT ATA    24